United States Patent [19]
Kawataka et al.

[11] Patent Number: 5,969,183
[45] Date of Patent: Oct. 19, 1999

[54] PROCESS FOR PRODUCING ACETIC ACID FROM METHYL FORMATE

[75] Inventors: Futoshi Kawataka; Yoshikazu Shima; Kenichi Nakamura, all of Tsukuba, Japan

[73] Assignee: Mitsubishi Gas Chemical Company, Inc., Tokyo, Japan

[21] Appl. No.: 09/033,083

[22] Filed: Mar. 2, 1998

[30] Foreign Application Priority Data

Feb. 28, 1997 [JP] Japan ................................. 9-045926

[51] Int. Cl.$^6$ ........................... C07C 53/08; C07C 51/42
[52] U.S. Cl. ......................... 562/607; 562/606; 562/608
[58] Field of Search .................... 562/607, 606, 562/608

[56] References Cited

U.S. PATENT DOCUMENTS

| | | | |
|---|---|---|---|
| Re. 29,981 | 5/1979 | Isogai | 562/400 |
| 4,061,546 | 12/1977 | Singleton | 203/31 |
| 4,613,693 | 9/1986 | Ray | 562/517 |

*Primary Examiner*—Samuel Barts
*Assistant Examiner*—Rosalynd Keys
*Attorney, Agent, or Firm*—Pillsbury Madison & Sutro LLP

[57] ABSTRACT

Provided is a process for producing acetic acid by carrying out reaction of methyl formate in the presence of a Group VIII metal catalyst, at least one iodine compound, acetic acid and carbon monoxide, continuously drawing a reaction mixture from a reactor, introducing the reaction mixture into a flash distillation zone, separating an evaporated component and an unevaporated component, recycling the unevaporated component to the reaction zone, and obtaining acetic acid from the evaporated component, wherein formic acid and methyl formate are allowed to coexist in the flash distillation zone and/or the recycling zone. According to this process, no loss of methyl formate and formic acid is caused and only methyl formate is used as a starting material with basically requiring no supply of carbon monoxide.

3 Claims, 1 Drawing Sheet

PROCESS FOR PRODUCING ACETIC ACID FROM METHYL FORMATE

BACKGROUND OF THE INVENTION

The present invention relates to a process for producing acetic acid. More particularly, it relates to a process for producing acetic acid by the reaction of methyl formate as a starting material under pressure of carbon monoxide. Acetic acid is a basic chemical which is industrially used as starting materials for acetic esters, acetic anhydride, vinyl acetate and terephthalic acid.

Oxidation of acetaldehyde, oxidation of naphtha or olefins, and, furthermore, preparation from methanol and carbon monoxide are known as processes for the industrial production of acetic acid. As the process of reacting methanol with carbon monoxide, there are widely known processes, e.g., so-called high-pressure carbonyl process using cobalt catalysts and so-called Monsanto process carried out under low pressures using rhodium catalysts. However, according to these conventional techniques comprising carbonylation of methanol, high purity carbon monoxide is practically required in an amount more than the amount required for acetic acid to be produced. Monsanto process has a defect that it requires plant cost for generation of carbon monoxide nearly equal to plant cost for carbonylation step.

In the production of acetic acid by carbonylation reaction of methanol, coexistence of water is necessary, and even if water concentration in the reaction mixture is reduced to not more than 5% by weight as shown in the improved process, the water gas shift reaction which produces carbon dioxide and hydrogen from carbon monoxide and water cannot be completely inhibited, and, besides, for obtaining product acetic acid, much energy is needed for separation of water in the distillation step. Further defect is that a perfect mixing tank type reactor having a stirrer is used in the carbonylation reaction of methanol for the acceleration of dissolution of carbon monoxide into a liquid phase catalyst, and, hence, power for stirring is necessary.

Reaction mechanism of the carbonylation reaction of methanol is considered as shown below. As can be seen from the equation (3) mentioned below, it is a reaction consuming carbon monoxide.

$$CH_3OH + CH_3COOH \rightarrow CH_3COOCH_3 + H_2O \quad (1)$$

$$CH_3COOCH_3 + HI \rightarrow CH_3I + CH_3COOH \quad (2)$$

$$CH_3I + CO \rightarrow CH_3COI \quad (3)$$

$$CH_3COI + H_2O \rightarrow CH_3COOH + HI \quad (4)$$

On the other hand, for the production of acetic acid by heating methyl formate under pressure of carbon monoxide, there are known a process which uses rhodium as catalyst (JP-A-49-3513) and a process which uses a homogeneous catalyst system comprising rhodium metal atom and a mixture of lithium iodide and methyl iodide (JP-A-60-149542).

Reaction mechanism of this reaction is considered as follows.

$$HCOOCH_3 + CH_3COOH \rightarrow CH_3COOCH_3 + HCOOH \quad (5)$$

$$CH_3COOCH_3 + HI \rightarrow CH_3COOH + CH_3I \quad (6)$$

$$CH_3I + CO \rightarrow CH_3COI \quad (7)$$

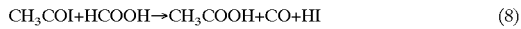
$$CH_3COI + HCOOH \rightarrow CH_3COOH + CO + HI \quad (8)$$

It can be seen from the equations (7) and (8) that being different from the process of carbonylation of methanol, consumption amount and production amount of carbon monoxide are the same when methyl formate is used as a starting material. Since the reaction having such features is utilized, in the process for the production of acetic acid from methyl formate, the apparatus for generating carbon monoxide can be of very small-scale for maintaining the carbon monoxide atmosphere in the reaction system.

The inventors found a process for producing acetic acid using methyl formate as a starting material which is released from the restriction on equipment for producing high purity carbon monoxide and, besides, minimizes the energy cost required for purification of product acetic acid and thus filed a patent application thereon (JP-Appln. 8-270855). According to this process, it has become possible to sufficiently increase space time yield and conversion which have hitherto been problems to be solved and minimized by-production of formic acid and methyl acetate which are convertible to methyl formate and acetic acid by altering reactors and reaction forms to those suitable for isomerization reaction of methyl formate. This invention can provide a process for the production of acetic acid which is economical over the Monsanto process and the improved Monsanto process.

However, though some processes for producing acetic acid using only methyl formate as a starting material have been reported by the inventors and others, there have been no examples of constructing a process which includes separation of the produced acetic acid and recycling of reaction mixture and catalyst. It has been considered that since there are many similarities between the reaction mechanism of production of acetic acid by carbonylation of methanol and the reaction mechanism of producing acetic acid by isomerization of methyl formate, carbonylation of methanol and isomerization of methyl formate are similar also in the production processes thereof, but it has not been elucidated that there are problems peculiar to the isomerization process of methyl formate.

For the purpose of establishment of a process, the inventors have conducted investigation using apparatuses which are for flash distillation and recycling of reaction mixtures, in addition to reactors. As a result, it has become clear that in some cases, decomposition of methyl formate which is a starting material and formic acid which is a reaction intermediate takes place in the flash distillation zone and the recycling zone, respectively. Unless decomposition of these compounds are inhibited, not only the features of the process for producing acetic acid by isomerization of methyl formate are lost, but also sometimes the process per se cannot be materialized.

SUMMARY OF THE INVENTION

The object of the present invention is to find a method for inhibiting decomposition of methyl formate which is a starting material and formic acid which is a reaction intermediate in the flash distillation zone and recycling zone in the production of acetic acid by isomerizing methyl formate, thereby to establish a process for producing acetic acid using only methyl formate as a starting material.

BRIEF DESCRIPTION OF DRAWINGS

In FIG. 1, reference numerals indicate the following.

Figure 1:
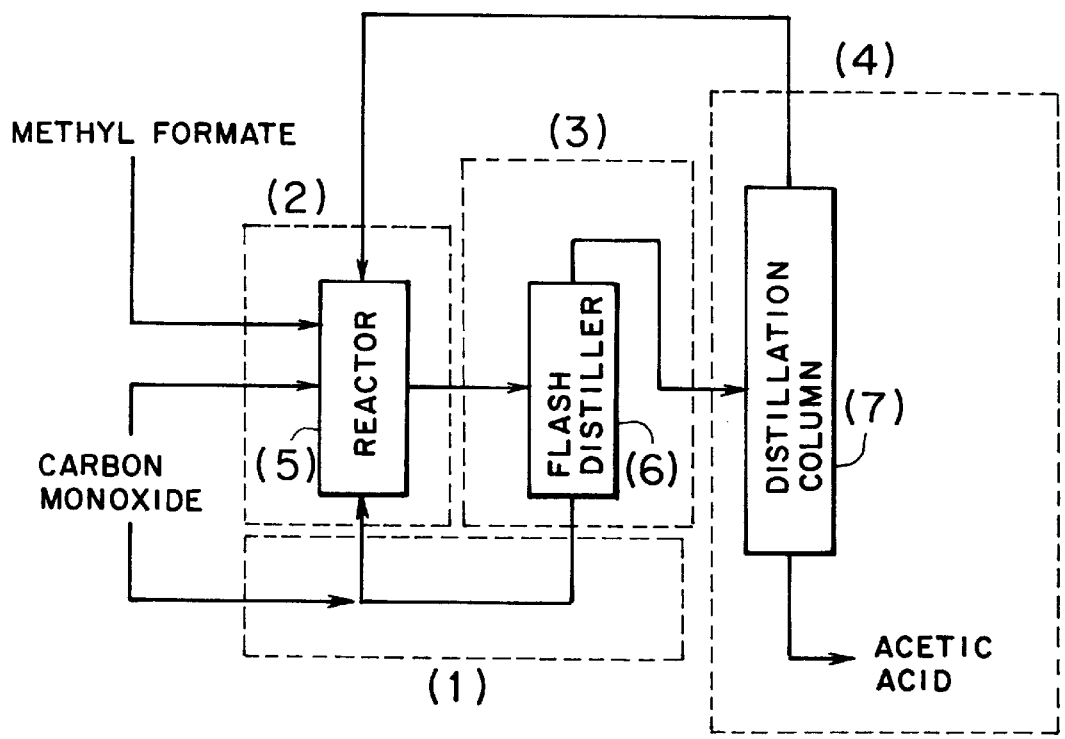
FIG. 1 is a diagram of the process of the present invention.

(1): Recycling zone
(2): Reaction zone
(3): Flash distillation zone
(4): Purification zone
(5): Reactor
(6): Flash distiller
(7): Distillation column In FIG. 2, reference numerals indicate the following.

(1): Catalyst solution tank
(2): Reactor
(3): Flash distiller
(4): Condenser
(5): Crude product tank
(6): Solution feeding pump
(7): Distillation column
(8): Solution feeding pump

DESCRIPTION OF THE INVENTION

The inventors have conducted investigation of a production process of acetic acid by the isomerization of methyl formate using apparatuses which are for flash distillation and recycling of reaction mixtures. As shown in FIG. 1, the process for producing acetic acid by isomerization of methyl formate comprises a reaction zone (2), a flash distillation zone (3), a recycling zone (1) and a purification zone (4).

As explained below, methyl formate as a starting material, a Group VIII metal catalyst, a solution containing at least one iodine compound and carbon monoxide are continuously fed to the reactor, and a reaction mixture is continuously drawn from the reactor.

The catalyst used for producing acetic acid from methyl formate comprises a combination of a Group VIII metal catalyst with at least one iodine compound. The Group VIII metals here include rhodium, iron, ruthenium, osmium, cobalt, iridium, nickel, palladium and platinum. Among them, rhodium is preferred. The iodine compounds in the present invention include iodine, methyl iodide, lithium iodide, sodium iodide, potassium iodide, cesium iodide and the like. The iodine compound of the catalyst used suitably in the present invention is a combination of methyl iodide with lithium iodide. That is, combination of rhodium with methyl iodide and lithium iodide is preferred as the catalyst used in the present invention.

In the isomerization reaction of methyl formate according to the present invention, formic acid and methyl acetate which are intermediates are produced by interesterification reaction between methyl formate and acetic acid. These formic acid and methyl acetate are recovered from the reaction mixture and circulated to the reactor. Formic acid and methyl acetate contained in the circulated solution added to the raw materials can return to methyl formate and acetic acid respectively, through inverse reaction of the interesterification reaction. In steady state, formic acid and methyl acetate keep a concentration at equilibrium state and are present in equal mol in the reactor. From the points of equipment scale of the circulation step and quantity of energy used, economically the most advantageous concentration of formic acid and methyl acetate in the reaction mixture is 0.1–10% by weight respectively.

The reaction temperature is within the range of 100–240° C. In the isomerization reaction of methyl formate carried out under substantially anhydrous condition, water gas shift reaction which rapidly proceeds at higher than 180° C. does not take place, being different from carbonylation of methanol. Therefore, reaction rate can be improved at 180° C. or higher. Especially preferred is 180–210° C.

The present invention is practiced in the presence of carbon monoxide. Carbon monoxide used is not necessarily pure. Inert gases such as carbon dioxide, nitrogen and methane in a slight amount are not inhibition factors. Partial pressure of carbon monoxide may be such that necessary to maintain rhodium carbonyl complex. Since there is substantially no loss of carbon monoxide due to the shift reaction in the isomerization reaction of methyl formate carried out under substantially anhydrous condition, only the amount of carbon monoxide which is dissolved in the produced solution and discharged from the reaction system should be supplied, and, thus, it can be mostly ignored. The partial pressure of carbon monoxide necessary in the present invention is 0.1–50 kgf/cm$^2$. The total pressure of reaction is 1–100 kgf/cm$^2$, preferably 10–50 kgf/cm$^2$.

The present reaction can be performed by batch reaction process or continuous reaction process, but the continuous reaction process is preferred. The continuous reaction process is most preferably carried out in piston flow manner. The reactor can be not only a mixing tank type, but also columnar type or tubular type.

The reaction mixture drawn from the reactor is continuously introduced into flash distillation zone and flash distilled. The component evaporated here is introduced into the purification zone directly or after being condensed in a condenser. Acetic acid is drawn from purification zone as a product, and the remainder is returned to the reactor. The bottoms, which means a solution drawn from the bottom of flash distiller after distillation, are returned to the reactor through a recycling zone. In the recycling zone, there are, if necessary, a tank temporarily storing a catalyst solution in addition to solution supplying piping and solution feeding pump.

In the recycling zone, formic acid and methyl formate are allowed to coexist, because methyl formate inhibits decomposition of formic acid.

It is known that formic acid readily decomposes into carbon dioxide and hydrogen at relatively high temperatures (equation 9).

$$HCOOH \rightarrow CO_2 + H_2 \tag{9}$$

Since carbon dioxide and hydrogen cannot be finally converted to acetic acid, the side reaction of the equation (9) must be inhibited as much as possible.

Furthermore, formic acid sometimes decomposes into carbon monoxide and water even at relatively low temperatures in the presence of Group VIII metals (equation 10).

$$HCOOH \rightarrow CO + H_2O \tag{10}$$

On the other hand, the inventors have confirmed that water and carbon monoxide react with methyl formate in the presence of Group VIII metal catalysts to be converted to acetic acid and formic acid (equations 11, 12).

$$HCOOCH_3 + H_2O \rightarrow HCOOH + CH_3OH \tag{11}$$

$$CH_3OH + CO \rightarrow CH_3COOH \tag{12}$$

As the reactions of equations (10), (11) and (12) can be simultaneously allowed to proceed with inhibiting the reaction of equation (9), decomposition of formic acid can be inhibited as a whole because water and carbon monoxide are reconverted to formic acid.

The effect of inhibiting decomposition of formic acid is seen even with low amount of methyl formate, but the effect is conspicuous when amount of methyl formate is 0.1 equivalent or more to one equivalent of formic acid.

In realization of the inhibition method, it is necessary that reaction rates of equations (11) and (12) are higher than that of equation (10). If the reaction of equation (10) proceeds more rapidly than the reactions of equations (11) and (12) to produce carbon monoxide in a large amount, pressure in the apparatus increases and carbon monoxide must be purged out of the system for safety. In this case, water stays in the apparatus and hinders the production of acetic acid. If the water is retained as it is, the process cannot be realized. Therefore, a large quantity of energy must be introduced to separate and abolish water in the flash distillation zone and purification zone, respectively, and, moreover, supplying power of the apparatus for the production and supplying carbon monoxide must be increased to supply carbon monoxide in an amount equal to the amount of the purged carbon monoxide to the apparatus for producing acetic acid. These measures are also not desired for simplification of process and energy saving. Therefore, it is preferred to allow formic acid and methyl formate to coexist sufficiently not only in the reactor, but also in the flash distillation zone and the recycling zone.

However, methyl formate is lower in boiling point than formic acid and, hence, is mostly evaporated in the flash distillation zone and transfered into the purification zone. Thus, ratio of methyl formate to formic acid in the recycling zone is apt to be too low. Depending on reaction conditions or flash distillation conditions, methyl formate is sometimes not present substantially in the bottoms of the flash distillation zone. Accordingly, it is necessary to suitably control the operation conditions of the flash distillation zone or to further add methyl formate to the recycling zone.

The inventors have further confirmed that there are conditions under which methyl formate decomposes at a temperature higher than room temperature in the presence of a Group VIII metal to be converted to carbon dioxide and methane (equation 13).

$$HCOOCH_3 \rightarrow CO_2 + CH_4 \qquad (13)$$

Carbon dioxide and methane must be wasted because they cannot be converted to acetic acid, and this is a loss for the process of producing acetic acid.

The inventors have found that when carbon monoxide is introduced into a solution containing a Group VIII metal and methyl formate, decomposition of methyl formate is inhibited to cause decrease in the amounts of carbon dioxide and methane produced. Accordingly, it is preferred to add carbon monoxide not only to the reactor, but also to the flash distillation zone and the recycling zone. The pressure can be 0.1 kgf/cm² or higher, but at the same temperature, the higher the pressure of the added carbon monoxide is, the greater the effect to inhibit the decomposition of methyl formate is. Moreover, methyl formate becomes more difficult to decompose with decrease in temperatures. For example, with addition of carbon monoxide in an amount of 1.5 kgf/cm² at 130° C. and 7 kgf/cm² at 190° C., decomposition of methyl formate can be nearly completely inhibited.

Being different from the recycling zone, since in the flash distillation zone, carbon monoxide or methyl formate is evaporated, it is sometimes difficult to maintain at high level the concentration of these components dissolved in it. Nevertheless, inhibition of decomposition of formic acid with methyl formate and that of methyl formate with carbon monoxide are sometimes encountered.

Thus, the inventors have conducted investigation on various operation conditions in the flash distillation zone to find that decomposition of methyl formate and formic acid can also be inhibited by suitably selecting the operation conditions in the following manner. That is, it is effective to carry out the operation by setting the temperature of the flash distiller at 180° C. or lower, preferably 110–150° C. and with an average residence time of the produced solution of 30 minutes or less in the state of coexistence of methyl formate and formic acid.

Furthermore, when flash distillation is carried out with introducing carbon monoxide stream into the flash distiller in the state of coexistence of methyl formate and formic acid and with maintaining the carbon monoxide partial pressure, the average residence time can be prolonged with inhibiting decomposition of methyl formate and formic acid in the flash distiller. In this case, since evaporation in the flash distiller is accelerated by the gas, the flash distiller can be made smaller. Temperature of the flash distiller can be 180° C. or lower, preferably 100–160° C.

The present invention will be explained in more detail by the following nonlimiting examples.

[Explanation of Reaction Apparatus and Operation]

Figure 2:
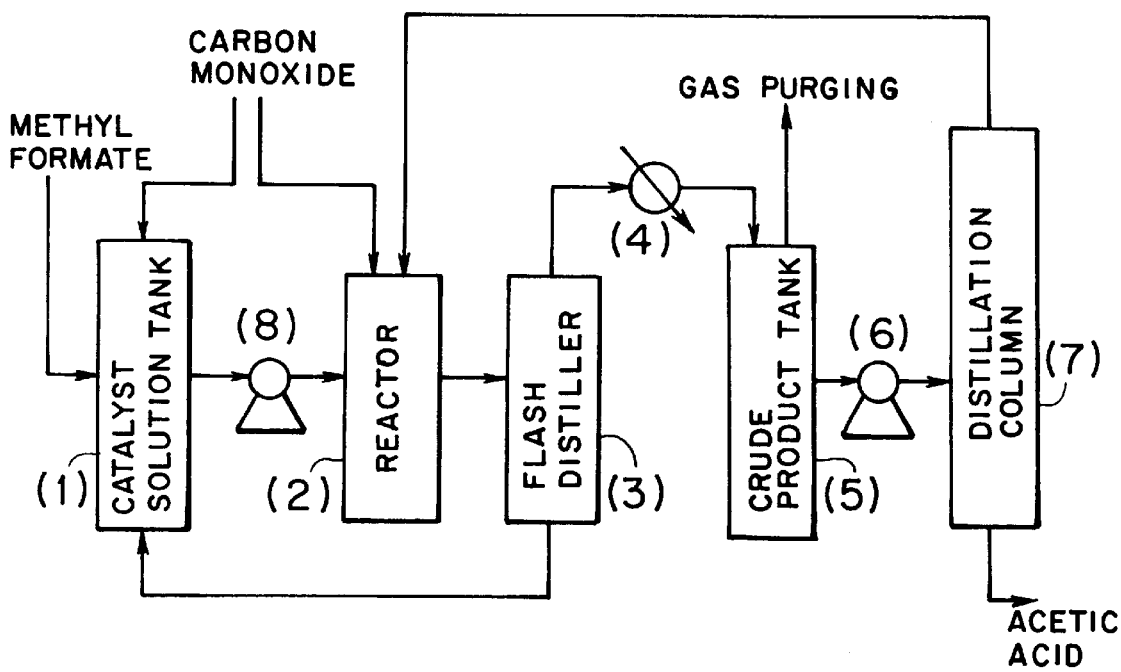
FIG. 2 is a schematic view of the apparatus used in Examples.

As shown in FIG. 2, the reaction apparatus comprises a carbon monoxide supplying apparatus, a reactor (2), a flash distiller (3), a condenser (4), a catalyst solution tank (1), a crude product tank (5), a distillation column (7), solution feeding pumps (6) and (8), and a piping.

A carbonylation reactor including a pressure reactor (made of zirconium and having an internal volume of 500 mL) provided with a stirrer was previously filled with a raw material solution containing 15.6% by weight of methyl formate, 11.3% by weight of methyl iodide, 61.7% by weight of acetic acid, 1.5% by weight of formic acid, 2.2% by weight of methyl acetate, 5.1% by weight of lithium iodide and 750 ppm of rhodium, and a reaction mixture in an amount equal to the feed amount of raw material solution was drawn simultaneously with feeding the raw material solution keeping the amount of residence solution at 200 mL by sensing the liquid level in the reactor with supplying carbon monoxide so as to maintain a pressure of 30 kgf/cm². Furthermore, heating and removal of heat were carried out so as to keep solution temperature at 190° C.

A reaction mixture flowed into the flash distiller from the reactor and was flash distilled. Operation of flash distillation was carried out at given temperature, pressure and average residence time. The bottoms contained catalyst components and were introduced into a catalyst tank from the bottom of the flash distiller. The components evaporated in the flash distiller were condensed in the condenser and then introduced into the crude product tank. Uncondensable gases such as carbon monoxide were purged.

The solution stored in the crude product tank was introduced into the distillation column and distilled, and, thereafter, acetic acid was drawn as a product. Components other than acetic acid were returned to the reactor.

The catalyst solution tank was kept at a given temperature and methyl formate was added in addition to the solution discharged from the bottom of flash distiller. Furthermore, this tank was kept under given atmosphere and pressure. The solution in this tank was recycled to the reactor by the solution feeding pump.

EXAMPLE 1

The raw material solution was fed into the reactor at 800 g/hr, followed by operating the reactor. The solution discharged from the reactor contained 1.7% by weight of methyl formate, 11.3% by weight of methyl iodide, 75.6% by weight of acetic acid, 1.5% by weight of formic acid, 2.2% by weight of methyl acetate, 5.1% by weight of lithium iodide and 750 ppm of rhodium. Molar ratio of methyl formate to formic acid was methyl formate/formic acid=1.2. The flash distillation was carried out at 130° C. and with an average residence time of 4 minutes.

A condensate was flowed into the crude product tank from the top of the flash distiller at a rate of 217 g/hr, and it contained 30.5% by weight of methyl iodide, 3.6% by weight of methyl acetate, 59.0% by weight of acetic acid, 2.2% by weight of formic acid and 2.1% by weight of methyl formate.

Uncondensable gas was purged at 0.8 L/hr.

The bottoms of the flash distiller were introduced into a catalyst solution tank at 583 g/hr and it contained 4.7% by weight of methyl iodide, 0.5% by weight of methyl acetate, 87.2% by weight of acetic acid, 1.1% by weight of formic acid, 0.6% by weight of methyl formate and 1030 ppm of rhodium.

When weights of methyl formate and formic acid flowing into the flash distiller were compared with weights of methyl formate and formic acid flowing into the crude product tank and the catalyst solution tank, it was found that 1.3 mol % of methyl formate was decomposed into methane and carbon dioxide in the flash distiller. Furthermore, production of water was not seen, and, thus, decomposition of formic acid did not take place.

EXAMPLE 2

The procedure of Example 1 was repeated using the same apparatus, except that the average residence time in the flash distiller was 40 minutes. As a result, 9.9 mol % of methyl formate flowing into the flash distiller from the reactor decomposed into methane and carbon dioxide. Furthermore, it was found that 9.8 mol % of formic acid decomposed in consideration of material balance of amount of formic acid consumed, amount of methyl formate consumed and amount of water produced.

EXAMPLE 3

The procedure of Example 1 was repeated, except that carbon monoxide was supplied from the bottom of the flash distiller at 6 L/hr and the average residence time was 40 minutes. As a result, 1.1 mol % of methyl formate flowing into the flash distiller from the reactor decomposed into methane and carbon dioxide. Thus, even when the residence time is longer, decomposition of methyl formate can be inhibited by allowing carbon monoxide to coexist.

EXAMPLE 4

A catalyst solution was prepared by adding methyl formate to the bottoms of the flash distiller obtained in Example 1. The catalyst solution contained 14.6% by weight of methyl formate, 4.7% by weight of methyl iodide, 73.0% by weight of acetic acid, 0.5% by weight of methyl acetate, 1.1% by weight of formic acid, 6.1% by weight of lithium iodide and 900 ppm of rhodium (methyl formate/formic acid=10.2 mol/mol). This solution was introduced into a catalyst solution tank kept at 130° C. and at a fill up ratio of 20%, and carbon monoxide was added to adjust the pressure to 2 kgf/cm$^2$, followed by storing the solution for one week. The pressure did not change, and hydrogen, carbon dioxide and methane were not detected from the gaseous phase portion. The solution in the tank contained 9.3% by weight of methyl formate, 4.7% by weight of methyl iodide, 4.8% by weight of methyl acetate, 3.8% by weight of formic acid and 71.3% by weight of acetic acid.

Interesterification reaction between methyl formate and acetic acid took place, but production of carbon dioxide and methane due to decomposition was inhibited. Moreover, it was found that 2.8 mol % of formic acid decomposed in consideration of material balance of amount of formic acid consumed, amount of methyl formate consumed and amount of water produced.

EXAMPLE 5

Bottoms (methyl formate/formic acid=0.4 mol/mol) of flash distiller obtained in Example 1 was introduced into a catalyst solution tank kept at 130° C. and at a fill up ratio of 20%, and carbon monoxide was added to adjust the pressure to 2 kgf/cm$^2$, followed by storing for one week. The pressure increased to 2.2 kgf/cm$^2$. Hydrogen, carbon dioxide and methane were not detected from the gaseous phase portion. The solution in the tank contained 0.2% by weight of methyl formate, 4.7% by weight of methyl iodide, 87.5% by weight of acetic acid, 0.5% by weight of methyl acetate and 1.0% by weight of formic acid.

It was found that production of carbon dioxide and methane due to decomposition of methyl formate was inhibited. Moreover, it was found that 12 mol % of formic acid decomposed in consideration of material balance of amount of formic acid consumed, amount of methyl formate consumed and amount of water produced.

EXAMPLE 6

The procedure of Example 5 was repeated, except that air was introduced into the tank in place of carbon monoxide. The pressure in the catalyst solution tank increased to 3.7 kgf/cm$^2$. The gaseous phase contained 2.4 vol % of methane, 2.4 vol % of carbon dioxide and 11.8 vol % of carbon monoxide. The solution in the tank contained 0.1% by weight of methyl formate, 4.7% by weight of methyl iodide, 88.1% by weight of acetic acid, 0.5% by weight of methyl acetate, 0.4% by weight of formic acid and 0.4% by weight of water.

It was found that 37 mol % of methyl formate decomposed in consideration of amounts of methane and carbon dioxide produced. Moreover, it was found that 61 mol % of formic acid decomposed into water and carbon monoxide in consideration of material balance of amount of formic acid consumed, amount of methyl formate consumed and amount of water produced.

Comparative Example 1

Bottoms of flash distiller comprising 3.6% by weight of methyl iodide, 138.3% by weight of acetic acid, 1.2% by weight of formic acid, 7.0% by weight of lithium iodide and 1030 ppm of rhodium (containing no methyl formate) were introduced into a catalyst solution tank kept at 130° C. and at a fill up ratio of 20%, and carbon monoxide was added to adjust the pressure to 2 kgf/cm$^2$, followed by storing for one week. The pressure increased to 3.7 kgf/cm$^2$. Carbon dioxide and hydrogen were not detected from the gaseous phase portion. The liquid phase portion contained 3.6% by weight of methyl iodide, 88.4% by weight of acetic acid and 0.5% by weight of water.

Formic acid completely decomposed to water and carbon monoxide and disappeared.

EXAMPLE 7

[Preparation of catalyst raw material solution]

In a 5 L autoclave made of zirconium and equipped with a stirrer were charged with 2400 g of acetic acid, 573 g of anhydrous lithium iodide and 39.6 g of anhydrous rhodium triiodide. Therein was charged 5 $kgf/cm^2$ of carbon monoxide, followed by carrying out purging to replace gases in the system with carbon monoxide. This operation was carried out twice. Then, 2 $kgf/cm^2$ of carbon monoxide was charged therein at room temperature, and temperature was raised to 130° C. with stirring to perform reaction at 130° C. for 1 hour to produce soluble rhodium carbonyl. Thus, a catalyst raw material solution was obtained.

In the following examples, necessary components such as methyl formate were added to the catalyst raw material solution to prepare a raw material solution.

Necessary components such as methyl formate were added to the catalyst raw material solution to prepare 10 kg of a raw material solution comprising 17.0% by weight of methyl formate, 15.0% by weight of methyl iodide, 0.86% by weight of methyl acetate, 61.5% by weight of acetic acid, 0.53% by weight of formic acid, 5.0% by weight of lithium iodide, 750 ppm of Rh and 50 ppm of water.

An autoclave made of zirconium was prepared which had an inner diameter of 4 cm and a height of 20 cm and was equipped with a liquid level sensor, a thermometer, a gas blowing nozzle and a stirrer.

An apparatus was made so that when the raw material solution is fed from the top of the reactor, a reaction mixture can be drawn from a drawing control valve at the bottom of the reactor and introduced into a cooling column upon amount of solution reaching 200 ml according to the liquid level. sensor, and, furthermore, carbon monoxide in an amount corresponding to the amount of purged gas can be supplied from the gas blowing nozzle at the bottom of the reactor through a flow control device.

Without stirring, carbon monoxide was supplied so that the total pressure in the reactor reached a dwell pressure of 30 $kgf/cm^2$ and the raw material solution was fed at a rate of 900 g/hr at a reaction temperature of 195° C.

The reaction mixture was introduced to a cooling column, and then drawn from the bottom of the cooling column upon reaching steady state, and analyzed. The product solution contained 1.70% by weight of methyl formate, 15.0% by weight of methyl iodide, 0.86% by weight of methyl acetate, 76.8% by weight of acetic acid, 0.53% by weight of formic acid, and 5.0% by weight of lithium iodide. The product solution was obtained at a rate of 900 g/hr, and conversion of methyl formate was 90 mol %.

Amounts of formic acid and methyl acetate produced and consumed were the same, and thus when formic acid and methyl formate in the product solution were recycled to the raw material system, by-products could be regarded not to be produced. Selectivity of methyl formate to acetic acid was at least 99%, and unaltered methyl formate was recycled, if necessary, to the raw material system. Space time yield was 688 g-acetic acid/L·hr.

During the reaction for 10 hours with passing the solution, 2 L of purge gas was obtained from the top of the cooling column, and as a result of analysis, the gas contained 0.28 vol % of carbon dioxide, 0.08 vol % of hydrogen and 0.06 vol % of methane.

EXAMPLE 8

The same raw material solution as in Example 7 were prepared.

The same apparatus as used in Example 7 was used, except that it was reformed so that carbon monoxide could be supplied to the gaseous phase portion of the top part of the reactor.

Without stirring, carbon monoxide was supplied so that the total pressure in the reactor reached a dwell pressure of 34 $kgf/cm^2$ and the raw material solution was fed at a rate of 1300 g/hr at a reaction temperature of 205° C.

The product solution was drawn from the bottom of the cooling column upon reaching steady state, and analyzed. The product solution contained 1.70% by weight of methyl formate, 15.0% by weight of methyl iodide, 0.86% by weight of methyl acetate, 76.8% by weight of acetic acid, 0.53% by weight of formic acid and 5.0% by weight of lithium iodide. The product solution was obtained at a rate of 1300 g/hr.

Conversion of methyl formate was 90 mol %, and by-products could be regarded not to be produced as same as in Example 7. Space time yield was 994 g-acetic acid/L·hr.

During the reaction for 7 hours with passing the solution, 3 L of purge gas was obtained from the top of the cooling column, and as a result of analysis, the gas contained 0.28 vol % of carbon dioxide, 0.08 vol % of hydrogen and 0.06 vol % of methane.

What is claimed is:

1. A process for producing acetic acid which comprises carrying out an isomerization reaction of methyl formate to acetic acid in the presence of a Group VIII metal catalyst, at least one iodine compound and carbon monoxide, in a piston flow manner, in a reaction zone continuously drawing a reaction mixture into a flash distillation zone, separating an evaporated component from an unevaporated component, and recycling, in a recycling zone, the unevaporated component to the reaction zone, wherein formic acid as an intermediate, carbon monoxide and methyl formate are allowed to coexist in the flash distillation zone and/or the recycling zone.

2. A process according to claim 1, wherein a rhodium catalyst is used as the Group VIII metal catalyst.

3. A process according to claim 1, wherein flash distillation is carried out with an average residence time of 30 minutes or less and at a temperature of 180° C. or lower in the flash distillation zone.

* * * * *